US010234940B2

(12) United States Patent
Mardanbegi et al.

(10) Patent No.: US 10,234,940 B2
(45) Date of Patent: Mar. 19, 2019

(54) GAZE TRACKER AND A GAZE TRACKING METHOD

(71) Applicant: ITU Business Development A/S, Copenhagen S (DK)

(72) Inventors: Diako Mardanbegi, Copenhagen (DK); Dan Witzner Hansen, Olstykke (DK)

(73) Assignee: ITU Business Development A/S, Copenhagen S. (DK)

( * ) Notice: Subject to any disclaimer, the term of this patent is extended or adjusted under 35 U.S.C. 154(b) by 0 days.

(21) Appl. No.: 15/548,506

(22) PCT Filed: Feb. 4, 2016

(86) PCT No.: PCT/EP2016/052343
§ 371 (c)(1),
(2) Date: Aug. 3, 2017

(87) PCT Pub. No.: WO2016/124668
PCT Pub. Date: Aug. 11, 2016

(65) Prior Publication Data
US 2018/0239423 A1    Aug. 23, 2018

(30) Foreign Application Priority Data
Feb. 4, 2015   (DK) ................................. 201570064

(51) Int. Cl.
*G06K 9/00*  (2006.01)
*G06F 3/01*  (2006.01)
(Continued)

(52) U.S. Cl.
CPC .............. *G06F 3/013* (2013.01); *A61B 3/113* (2013.01); *G02B 27/0172* (2013.01); *G06T 7/74* (2017.01);
(Continued)

(58) Field of Classification Search
CPC ........................... G06F 3/013; G06K 9/00597; G06K 9/00604; G06T 2207/3004
See application file for complete search history.

(56) References Cited

U.S. PATENT DOCUMENTS 4,848,340 A    7/1989   Bille et al.
6,659,611 B2   12/2003  Amir et al.
(Continued)

FOREIGN PATENT DOCUMENTS

WO    00/26713 A1    5/2000
WO    10/003410 A1   1/2010
(Continued)

*Primary Examiner* — Wesley J Tucker
(74) *Attorney, Agent, or Firm* — Snyder, Clark, Lesch & Chung, LLP

(57) ABSTRACT

A gaze tracker and a computer-implemented method for gaze tracking, comprising the steps of: recording video images of a being's eye such that an eye pupil and a glint on the eye ball caused by a light source ( ) are recorded; processing the video images to compute an offset between the position of the predetermined spatial feature and a predetermined position with respect to the glint; by means of the light source such as a display, emitting light from a light pattern at a location selected among a multitude of preconfigured locations of light patterns towards the being's eye; wherein the location is controlled by a feedback signal; controlling the location of the light pattern from one location to another location among the predefined locations of light patterns, in response to the offset, such that the predetermined position with respect to the glint caused by the light source tracks the predetermined spatial feature of the being's eye; wherein the above steps are repeated to establish a control loop with the location of the light pattern being controlled via the feedback signal.

20 Claims, 6 Drawing Sheets

(51) Int. Cl.
*A61B 3/113* (2006.01)
*G06T 7/73* (2017.01)
*G02B 27/01* (2006.01)
*H04N 5/235* (2006.01)
*H04N 5/33* (2006.01)

(52) U.S. Cl.
CPC ............ *H04N 5/2354* (2013.01); *H04N 5/33* (2013.01); *G02B 2027/014* (2013.01); *G02B 2027/0138* (2013.01); *G06T 2207/10016* (2013.01); *G06T 2207/30041* (2013.01)

(56) References Cited

U.S. PATENT DOCUMENTS

| | | |
|---|---|---|
| 7,306,377 B2 | 12/2007 | Ellison |
| 7,686,451 B2 | 3/2010 | Cleveland |
| 8,878,749 B1 | 11/2014 | Wu et al. |
| 8,942,419 B1 | 1/2015 | Wu et al. |
| 9,625,723 B2* | 4/2017 | Lou ................ G02B 27/0172 |
| 9,775,512 B1* | 10/2017 | Tyler ..................... A61B 3/113 |
| 2003/0020707 A1* | 1/2003 | Kangas ................. G06F 3/011 |
| | | 345/418 |
| 2003/0098954 A1* | 5/2003 | Amir ...................... A61B 3/113 |
| | | 351/210 |
| 2004/0174496 A1* | 9/2004 | Ji ............................ G06F 3/013 |
| | | 351/209 |
| 2005/0175218 A1 | 8/2005 | Vertegaal et al. |
| 2008/0019127 A1 | 1/2008 | Dick et al. |
| 2010/0066975 A1* | 3/2010 | Rehnstrom .......... A61B 3/0008 |
| | | 351/210 |
| 2011/0085139 A1* | 4/2011 | Blixt ..................... A61B 3/113 |
| | | 351/209 |
| 2011/0170061 A1 | 7/2011 | Gordon |
| 2012/0294478 A1* | 11/2012 | Publicover ......... G06K 9/00604 |
| | | 382/103 |
| 2013/0050258 A1 | 2/2013 | Liu et al. |
| 2013/0178287 A1 | 7/2013 | Yahav |
| 2014/0002349 A1 | 1/2014 | Hansen |
| 2014/0009739 A1 | 1/2014 | Greco et al. |
| 2014/0055591 A1* | 2/2014 | Katz ....................... G06F 3/013 |
| | | 348/78 |
| 2014/0313308 A1* | 10/2014 | Wang ................. G06K 9/00604 |
| | | 348/78 |
| 2015/0242680 A1* | 8/2015 | Thukral ............. G06K 9/00335 |
| | | 348/78 |
| 2017/0123491 A1* | 5/2017 | Hansen .................. G06F 3/013 |

FOREIGN PATENT DOCUMENTS

| | | |
|---|---|---|
| WO | 2011/117776 A1 | 9/2011 |
| WO | 12/055444 A1 | 5/2012 |

* cited by examiner

GAZE TRACKER AND A GAZE TRACKING METHOD

Eye-tracking also denoted gaze estimation is an evolving technology that is becoming integrated in consumer products such as personal computers, laptop computers, tablet computers, smart phones, and other devices like for instance Wearable Computing Devices, WCDs comprising Head-Mounted Displays, HMDs.

However, there still exist problems in how to improve the accuracy of gaze trackers such that a user's gaze can be accurately and reliably computed.

RELATED PRIOR ART

U.S. Pat. No. 7,686,451 discloses a camera-based gaze tracker with a motorized gimbal mount for continuously pointing and focussing the camera on a user's eye. Thereby the camera moves as the user moves his head and it is thereby possible to increase the gaze tracker's tolerance to head motion. The camera is moved side-to-side and up-and-down via the motorized gimbal mount which is controlled by a direction-control loop that uses image processing software to track the movements of the eye. The direction-control loop is based on the eye tracker's eye image processing. As the head initiates movements, the image of the eye initially moves within the video image. As the eye moves away from the centre of the video image, commands are issued to the motorized gimbal to restore the eye to the centre of the screen. Thus, the camera's video image produces optical feedback to control the pitch and yaw of the gimbal mount whereon the camera sits.

There are alternative solutions which, contrary to this electro-mechanical solution, are based on advanced image processing methods which are highly accurate and largely invariant to head movements. However, it still remains a problem how to improve accuracy of a gaze tracker.

SUMMARY

There is provided a gaze tracker comprising:
an image processor configured to process video images of at least one eye of a being, wherein a predetermined spatial feature, such as the pupil, of the at least one eye and a glint caused by a light source is recorded, and to generate an offset signal representing an offset between a position of the predetermined spatial feature and a predetermined position with respect to the glint; and
a light source controller configured to output a control signal to a light source that is configured to emit a light pattern from a selectable position among a multitude of preconfigured positions towards the being's at least one eye;
wherein the light source controller is configured to move the light pattern, in response to a feedback signal; and
wherein the image processor and the light source controller are coupled in a control loop providing the feedback signal from the offset signal.

Consequently, the light source is arranged as a controllable component in a closed loop configuration. The light pattern emitted by the light source then moves as determined by the closed loop configuration to track the predetermined spatial feature, e.g. the pupil, and thus the eyeball as the eye moves. The position that the movable light pattern emanates from, or a reference position which is defined relative to a position of the movable light pattern, then is an estimate of the point-of-regard.

The light pattern may be moved about in a two-dimensional plane. The reference position is located in the two-dimensional plane as well. The two-dimensional plane may be defined by the light source; it may overlay a display screen such that a face of the display and a face of the light source largely span the same expanse.

Light emanates from the movable light pattern at or about an estimate of the point-of-regard. The point-of-regard is an estimate of where the being's gaze vector coincides with the light pattern.

It should be noted that in some situations the being's point-of-regard may remain fixed on a point while his/hers head is moved. In such a situation, the light pattern stays at the same position since the point-of-regard remains fixed. In situations where the user keeps his/hers head in a fixed position and moves his/hers eyes to move his/hers point-of-regard around, the light pattern will move correspondingly to follow the point-of-regard over time.

Conventionally, the relative offset between the pupil centre and a location of one or more glints is used to infer gaze in the form of a point-of-regard or a gaze vector. However, by the claimed gaze tracker, the relative offset between the pupil centre and the one or more glints is deliberately maintained to coincide or occur at a predetermined offset, despite of eye movements. The gaze vector or the point-of-regard is then computed or inferred from the location of the light pattern.

A significant advantage of the present invention is that the gaze error can be reduced or maintained at a relatively low level.

The light pattern is configured with a shape and expanse that is sufficiently geometrically well-defined that the gaze tracker by means of image processing can identify one or more well-defined points from the glint reflected on the eye. The expanse of the light pattern is sufficiently small to enable it to be moved about within a field-of-view of the beholder and sufficiently large to enable it be reliably detected as a glint as it is known in the art. The light pattern can be configured as a geometrical figure such as a 'dot' or a 'donut' or a 'ring' or a cross. The predetermined position with respect to the glint(s) can be the centre of the geometrical figure as reflected on the eye as one or more glints or a corner or any other point geometrically defined relative to the pattern. The geometrical figure can also be a pointed figure such as a triangle or an arrow. Alternatively, the light pattern can be configured as a pattern or constellation of multiple 'dots' or another shape e.g. arranged as corners of one or more imaginary rectangles or triangles or other polygons e.g. as the 'eyes' of domino pieces in the domino game. The selectable position of the light pattern is a position with a predefined geometrical relation with respect to the light pattern or constellation.

The being may also be denoted a user, a person, an individual or a beholder.

The light source is configured such that the multitude of preconfigured positions at which the light pattern can be positioned are arranged spatially on or at a plane or curved surface. The plane or curved surface may be arranged such that the plane is substantially at a right angle with respect to the beholder's gaze angle when (s)he is at an expected position. The expected position is e.g. 30 cm to 80 cm or longer in front of a display. In case the display sits close to the eye, such as in a HMD, the light source may be arranged to substantially extend with the display or be integrated therewith. The light source may also in the case of a HMD, be arranged along the edges of the display(s) or portions thereof.

The surface can be configured to cover a plane surface with predetermined dimensions or a curved surface covering a predetermined solid angle with respect to an expected position of the beholder's eye. The predetermine positions comprises discrete spatial positions arranged sufficiently close to achieve a desired spatial resolution of the gaze estimate e.g. corresponding to a pixel resolution of a display screen or a finer or coarser spatial resolution.

The light source can be arranged as a light display, wherein light emitting elements (e.g. light emitting diodes) are arranged in a matrix configuration in rows and columns (e.g. with more than 10 rows and more than 10 columns, e.g. more than 50 rows and more than 80 columns). The light elements may be arranged with a relatively narrow space or a relatively wide space between them compared to a dimension of a light element.

The light source controller receives the feedback signal and moves the light pattern in response to the feedback signal. The feedback signal is a signal in the closed loop that serves to couple the offset computed by the image processor, or a signal influenced by the offset, to the light source controller and to determine or at least influence the location of the light pattern. The feedback signal conveys information at a rate which may depend on the rate at which video images are delivered to the image processor and the rate at which the image processor is able to compute the offset. In some embodiments the offset is computed at a rate of about 10 to 120 times per second. The rate may be the same as a frame rate of one or more cameras capturing images of the user's at least one eye; wherein the frame rate it the rate at which the camera supplies images.

The light source controller is configured and arranged in the closed loop such that the position of the glint or glints tracks the predetermined spatial feature of the being's eye; e.g. the centre of the pupil. This means, other things being equal, that video images of the eye will show that the glint or glint(s) has/have a fixed position relative to the predetermined spatial feature of the being's eye; e.g. the centre of the pupil. However, in case of an initial phase of tracking the gaze, it may be observed that distance between the glint or a constellation of multiple glints and the predetermined spatial feature of the being's eye converges or swings in towards a gradually smaller value. The same observation may be made in case the eye moves relatively rapidly and the closed loop operates at a relatively low rate. The closed loop may be designed with a sufficient fast response to track so-called smooth pursuit eye-movements and at least some or all foreseeable saccadial eye movements. In other embodiments, the closed loop may be designed with a sufficient fast response to track so-called smooth pursuit eye-movements and to dampen its tracking of saccadial eye movements or at least relative fast saccadial eye movements. The response of the closed loop is determined i.a. by a filter property of the closed loop.

By means of the closed loop, the at least one eye of the being and the position of at least one glint on the eye are observed by the camera and the position of the light pattern emitted by the light source is then controlled with the aim of tracking the eye, e.g. tracking the pupil, by the light pattern.

The video images recorded by the camera may comprise video images or a sequence of still images. The video images are recorded by a video camera or a still image camera arranged with a field-of-view that is sufficiently wide to cover eye movements and in some embodiments additionally covering head movements.

In some embodiments the light source is configured as a first display comprising light emitting elements emitting infrared light and arranged regularly in an array structure extending over or along a preconfigured area. Since the light emitting elements emit infrared light, the light source can emit light in the beholder's field-of-view, and even in the centre thereof, for the purpose of estimating the point-of-regard or the gaze vector without disturbing the beholder's perceived view. The infrared light may comprise or be light at near-infrared wavelengths.

The first display can be arranged as a rectangular surface covering an area that is substantially similar to a computer display screen of a stationary computer, a laptop computer, a smart-phone, a smart-watch or a tablet computer. The first display may have a smaller as well as a larger area, usually with a height-to-width aspect ratio in the range 1:4 to 4:1.

The first display can be arranged as one or more elongated strips of one or more line arrays of light emitting elements or as a full or partial frame of light emitting elements. Such strips or frame can be arranged along two substantially perpendicular sides of a rectangular screen or surface or frame e.g. along all four edges of a rectangular element or along e.g. a top edge and a side edge. This has the advantage that the light pattern can follow the movement of the eye such that gaze estimation error can be minimized, and at the same time avoiding disturbing a line of sight to a screen or other object that the beholder looks at.

In some embodiments the preconfigured area is aligned with an area of a second display which is a computer display screen for displaying visible light.

Thereby the first display is aligned with the second display. When the first display and the second display have substantially the same dimensions, the displays may be aligned to overlap across their substantially entire expanse.

The first display may be arranged as a transparent display which is arranged as a layer on the second display, or vice versa. The first display or the second display or both may be a transparent or semi-transparent display such that a line of sight to a screen or other object that the beholder looks at is not significantly disturbed by the first display. The transparent display may be a transparent matrix display manufactured by NeoView™.

Alternatively, or additionally, the light elements of the first display are arranged adjacent to light elements of the second display. The light elements may be arranged alternately as in a chess pattern, wherein every second element is of the first display and every other element is of the second display. The light elements may also be arranged in other patterns wherein say 3-of-4 light elements belong to the second display and 1-of-4 elements belong to the first display. The light elements of the first display and the second display may also be arranged alternately in rows or columns, e.g. every second, third, fourth, fifth or sixth column or row may be light elements of the first display. Other ways of co-arranging light elements of the first display and the second display may also be used.

Thereby, the first display may be configured with a lower or higher resolution than the second display since the density of light elements of the two displays may be different. The light elements may be arranged in the substantially same plane.

In some embodiments the first display and the second display are integrated to form a dual wavelengths display. A dual wavelengths display is configured to emit predominantly visible light and predominantly non-visible light in a separately controllable manner.

The first display is configured to predominantly emit light in the infrared range. The second display is configured to emit visible light. However, the second display will inherently also emit at least some light energy in the infrared range. By proper configuration of the light intensity emitted by first display in the infrared range, at the location of the light pattern, the glint can be reliably captured by a camera sensitive to visible and infrared light. That is, detection of glints is not disturbed by visible light from the second display. By proper configuration is meant that the first display is configured to emit sufficiently high light intensity in the infrared range that glints can be reliably detected.

In some embodiments the first light source comprises a focussed light source and a controllable pivot mount arranged in combination to controllably, via the feedback signal, point focussed light onto a screen that is arranged in front of the eye such that a glint is observable on the eye. The light from the focussed light source is then reflected on the screen towards the at least one eye.

The focussed light source emits a light beam or light cone that is narrow and focussed on the display screen.

The screen may be arranged as a layer on the above-mentioned second display or the screen may be a surface thereof. The screen will then display a spot or pattern of light which is reflected towards the beholder's eye.

The focussed light source may be a light emitting diode such as a light emitting laser diode e.g. an infrared laser diode emitting light predominantly in the infrared range. For safety, the light intensity emitted by the focussed light source and impinging on the beholder's eye must be sufficiently low to avoid damage to the eye.

The light source itself and/or an optical system transmitting light from the light source to the screen is arranged to controllably point a light beam to the beholder's point-of-regard on the screen by means of the pivot mount.

Thereby the light source projects light, e.g. infrared light, onto the screen.

In some embodiments the gaze tracker is configured to filter the video images to identify one or more glints that are likely to origin from the light pattern, and wherein the predefined position relative the glint is computed relative to identified one or more glints that are identified to be likely to origin from the light pattern.

The gaze tracker may be configured to filter the video images based on non-linear filtering sometimes denoted glint-filtering.

Alternatively, or additionally, the filtering is based on deliberately superposing a predefined disturbing signal onto the feedback signal such that the light pattern and thus the glint is deliberately moved beyond tracking of eye movements. The gaze tracker is configured to identify the deliberate movement of the glint, corresponding to the movement induced by the predefined disturbing signal. This deliberate movement of the glint can be detected and used to identify the correct glint from other glints. This deliberate superposing of a predefined disturbing signal onto the feedback signal is applied to identify the correct glint during an initial phase or eye tracking or in case other glints spatially interferes with the correct glint.

In some embodiments the gaze tracker comprises a loop controller configured to filter the offset computed from processing the video images and outputting the feedback signal as a result of the filtering.

The closed loop gaze tracking operates at a rate determined by inter alia video frame rate of the video images and by processing rate of the image processor. However, the eye(s) may move at a speed completely independent therefrom. A loop filter may therefore be inserted in the closed loop to predict future values of the feedback signal or to low-pass filter previous values of the feedback signal to improve performance of the gaze tracker and its control loop. The loop filter also denoted a loop controller may comprise a configuration comprising one or more of: a proportional regulator, a proportional-integration regulator, a proportional-integration-differentiation regulator, a low-pass filter, and a Kalman filter. Thereby the temporal response of the estimated gaze to fast eye movements can be damped or enhanced to optimize performance under constraints set by response times of the light source, the video camera (frame rate) and computational speed of the image processor performing the image processing.

In some embodiments the gaze tracker comprises a camera arranged to record images of a being's eye such that a predetermined spatial feature of the being's eye and a glint caused by the controllable light source is recorded.

The camera is configured to be sensitive to light in the infrared range such that glints caused by infrared light sources can be detected.

The camera is arranged such that it points its image sensor or points its field of view towards the user's eye from a direction opposite his/hers face or such that the camera points its image sensor away from the beholder's face and towards a mirror or half-mirror that effectively gives the camera a field-of-view covering the eye.

In some embodiments the gaze tracker is configured to be worn as a wearable device and wherein the light source comprises light emitting elements arranged in an array structure extending over a preconfigured area which largely covers the field-of-view of the eye at least for some movements of the eye within the eye-socket.

Computing hardware for performing data processing tasks of the gaze tracker may be integrated in the body e.g. in the temples or sidebars or in a frame surrounding the visor.

In some embodiments the gaze tracker is configured to be worn as a wearable device, comprising: a scene camera with an image sensor; a screen, with a first layer and a second layer, arranged in front of the wearer's eye, with an inner sider facing towards the eye; wherein the light source is configured as a transparent display and arranged as the first layer of the screen; and wherein the second layer comprises a beam-splitting layer that splits light from at least some directions in front of the screen to impinge on the eye and on an image sensor of the scene camera; and wherein the scene camera is pointed towards the inner side of the screen.

The screen may be configured as the visor of a WCD.

The beam-splitting layer may be in the form of a so-called half-mirror.

A scene camera may record an image signal representing a scene in front of the beholder's head. The scene camera may point in a forward direction such that its field-of-view at least partially coincides or overlaps with the person's field of view e.g. such that the scene camera and the view provided to the person via the display have substantially the same field of view. When the scene camera is mounted on or integrated with a WCD it can be assured that the scene camera's field-of-view fully or partially covers or at least follows the person's field-of-view when (s)he wears the WCD.

In some embodiments an output indicative of a gaze vector or point-of-regard is generated from the feedback signal.

The feedback signal conveys information which is an indicator of a gaze point or gaze vector. The output may supply the feedback signal directly with an identical or similar data structure or via a data formatter that reformats a data structure of the feedback signal and/or via a data converter that converts the feedback signal into an appropriate signal. The output may be provided via a so-called Application Program Interface, API, or as a digital and/or analogue signal via a physical and/or virtual communications port.

In some embodiments the output is generated via a video camera arranged with a field-of-view at least partially covering the light source.

The light source displays the light pattern at a location representing the beholder's point-of-regard. The position of light emitted from the location of the light pattern is thereby indicative of the point-of-regard. This position can be computed from images of a video camera arranged with a field-of-view at least partially covering the light source and the output is generated accordingly to represent the point-of-regard.

There is also provided a computer-implemented method for gaze tracking, comprising the steps of:
  recording video images of a being's eye such that a predetermined spatial feature of the being's eye and a glint caused by a light source are recorded;
  processing the video images to compute an offset between the position of the predetermined spatial feature and a predetermined position with respect to the glint;
  by means of the light source, emitting light from a light pattern at a location selected among a multitude of preconfigured locations of light patterns towards the being's eye; wherein the location is controlled by a feedback signal;
  controlling the location of the light pattern from one location to another location among the predefined locations of light patterns, in response to the offset, such that the predetermined position with respect to the glint caused by the light source tracks the predetermined spatial feature of the being's eye;
  wherein the above steps are repeated to establish a control loop with the location of the light pattern being controlled via the feedback signal.

The method thereby adapts the spatial position, from which the light source emits light, to approach or coincide with the point-of-regard or the gaze vector. By controlling the location of the light pattern the light pattern is moved from one location to another location. The light pattern is moved by physically moving the light source as a car or carriage on a track; by pointing a light source on a screen by means of a pivot mount or gimbal mount or the like such that the light pattern is created by the light source's light cone; or by controlling which light elements to active among multiple light elements in a light display e.g. in a so-called dot-matrix display.

As mentioned above, the predetermined spatial feature of the eye may be the eye pupil, which is a feature that can be identified and located by conventional gaze estimation technology.

An image processor may be employed to compute the offset between the position of the predetermined spatial feature and a predetermined position with respect to the glint. The offset is also denoted an error vector or gaze error vector.

Since the gaze is tracked by a closed loop method which aims to intentionally minimize the offset, e.g. in terms of vector length, or make it intentionally approach or reach a predetermined offset value, the offset is also denoted an error vector or a pupil-glint vector. The offset is a two-dimensional vector or the length or a squared length of the vector. The offset is used as a feedback signal in the closed loop. The offset may thus be a vector that has a length and a direction. Alternatively, the feedback signal may represent the vector with the opposite direction i.e. rotated 180 degrees to directly represent the change in position of the light source required to minimize the error vector or offset.

In some embodiments, the closed loop is divided into two closed loops; one loop controlling movements of the light pattern in a horizontal direction and the other loop controlling movements of the light pattern in a vertical direction.

An estimate of the beholder's gaze may be generated or computed from the feedback signal. Alternatively, an estimate of the gaze may be generated by recording the light pattern emitted from the light source by means of a camera, which may also serve as a scene camera, and then performing image processing on the images recorded by the camera to identify the location of the light pattern. The location may be determined with respect to a field-of-view of the camera or it may be transformed to be determined with respect to another spatial reference.

In some embodiments the location of the light pattern is controlled via the feedback signal by sequentially addressing and activating different sets of light emitting elements among an array of light emitting elements arranged in a fixed structure.

Thereby, the light pattern can be moved dynamically without physically moving the light source by mechanical means.

By activating different sets of light emitting elements is understood that the light elements are turned 'on' from being 'off' or that their light intensity is significantly increased from a first level to a second level.

By sequentially addressing and activating different sets of light means that a set of light elements is activated to emit light form the light pattern at a first location and then the light pattern is moved to a second position by activating light elements constituting the light pattern at the second position. The light elements constituting the light pattern at the first location may be deactivated during, before or after the light pattern is moved.

By 'deactivated' is meant that sets of light emitting are turned 'off' from being 'on' or that their light intensity is significantly lowered from a first level to a second level.

The rate at which sequential addressing and activating is performed depends on a rate at which an estimate of the gaze is updated.

A trace of light patterns across several loop steps may be intentionally avoided by proper deactivation of the light elements such that at a given time instance activated light elements are restricted to a light pattern at one, two, three or a limited number of positions of light patterns; alternatively, a trace of light patterns may be intentionally desired by appropriately deactivating light elements subject to a delay of one or more loop steps or by gradually lowered light intensity of the light elements.

In some embodiments the computer-implemented method comprises filtering the offset computed from processing the video images by a loop controller and outputting the feedback signal as a result of the filtering.

In some embodiments the light pattern is emitted at an infrared wavelength and concurrently a visible user interface is displayed on a display screen.

In some embodiments the computer-implemented method comprises filtering the video images to identify one or more glints that are likely to origin from the light pattern, and computing a predefined position relative to the one or more glints that are identified.

The computer-implemented method can be performed by a mobile device, such as a head-worn computing device also denoted a Wearable Computing Device (WCD), e.g. shaped as spectacles or a spectacle frame configured with a scene camera arranged to view a scene in front of the person wearing the device, an eye-tracker e.g. using an eye camera arranged to view one or both of the person's eyes, a display arranged such that the user can view it when wearing the device, a computer unit and a computer interface for communicating with remote computer systems such as the Internet.

There is also provided a computer program product comprising program code means adapted to cause a data processing system to perform the steps of the method set forth above, when said program code means are executed on the data processing system.

The computer program product may comprise a computer-readable medium having stored thereon the program code means. The computer-readable medium may be a semiconductor integrated circuit such as a memory of the RAM or ROM type, an optical medium such as a CD or DVD or any other type of computer-readable medium.

There is also provided a computer data signal embodied in a carrier wave and representing sequences of instructions which, when executed by a processor, cause the processor to perform the steps of the method set forth above. The computer data signal may be a download signal. The computer data signal is communicated via a protocol such as the TCP/IP protocol.

Here and in the following, the terms 'eye tracker', 'gaze tracker', 'processor', 'image processor', 'computing hardware' etc. are intended to comprise any circuit and/or device suitably adapted and/or programmed to perform the functions described herein. In particular, the above term comprises general purpose or proprietary programmable microprocessors, Digital Signal Processors (DSP), Application Specific Integrated Circuits (ASIC), Programmable Logic Arrays (PLA), Field Programmable Gate Arrays (FPGA), special purpose electronic circuits, etc., or a combination thereof.

BRIEF DESCRIPTION OF THE FIGURES

A more detailed description follows below with reference to the drawing, in which.

DETAILED DESCRIPTION

Figure 1:
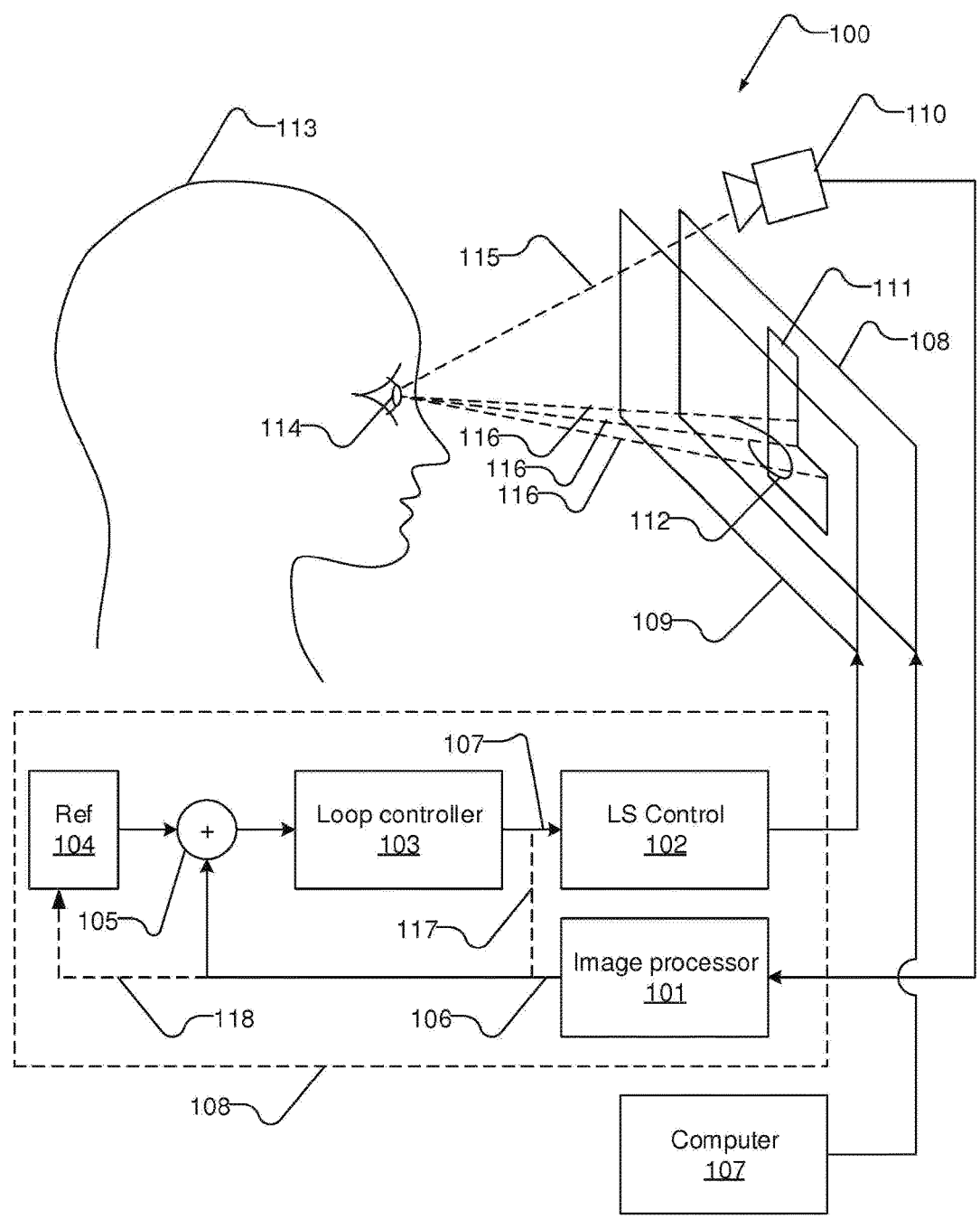
FIG. 1 shows a block diagram of a gaze tracking system.

FIG. 1 shows a block diagram of a gaze tracking system. The gaze tracking system 100 is shown in a side view with a human being 113, also denoted a user, that looks at a computer display 108 connected to a computer 107. As shown, and as an example, the display 108 displays a graphical object 111 shaped as a capital 'L'.

The human being 113 moves his gaze on the display 108 across different positions on the graphical object 111; this is illustrated for three different positions by dashed lines 116 and by a trace 112 across the positions. Light from the display 108 impinges on the pupil 114 of the user's right eye and causes so-called glints on the pupil 114. These glints are glints of visible light from the computer display 108.

The system 100 comprises a light source 109 configured as a transparent display in front of the computer display 108 and emitting light in the infrared range e.g in the near-infrared range. The light source is configured as a display and comprises light elements also denoted pixels e.g. light elements configured to emit infrared light. Infrared light from the light source 109 also impinges on the pupil 114 of the user's right eye and causes also so-called glints on the pupil 114. These glints are glints of infrared light from the light source 109.

The system 100 also comprises a camera 110 that is arranged in front of the user's face and aimed towards the face and in particular the pupil 114 as illustrated by dashed line 115. The camera 110 is configured to record video images or sequences of still images that capture the glints in an infrared light spectrum from the light source 109 and the pupil as it appears in the infrared light spectrum.

The light source 109 emits a pattern of light, e.g. in the form of an infrared 'dot' composed or one or more pixels, from a selectable position. The light source 109 is configured to receive a control signal from a light source controller 102 which controls the shape of the pattern of light and its position.

The camera 110 supplies images of the user's pupil 114 (of one of the eyes or of both) with one or more glints caused by the light source 109 to an image processor 101. The image processor 101 processes the images received form the camera 110 to compute or estimate an offset e.g. in the form or a two-dimensional vector between a geometrical centre of the pupil and a geometrical feature of one or more glints caused by the light source 109. This offset is an indicator of how to change the position of the infrared light 'dot' emitted by light source 109 such that a glint on the pupil 114 will occur right in the centre of the pupil or in any predetermined geometrical position relative to the pupil. Conventional image processing algorithms are available for computing such an offset. The offset may be output from the image processor 101 in the form of a signal denoted offset signal 106, which may be physical signal or a data item such as a software variable or other type of data object.

In some embodiments the image processor 101 outputs the offset e.g. as a two-dimensional vector value directly to the light source controller 102 as shown by connection 117 shown by a dashed line. Thereby the light source controller receives a feedback signal 107 which comprises the offset 106 computed by image processor 101.

The offset may be a pupil-to-glint vector. Then the light source controller 102 receives the offset, pupil-to-glint vector, and performs vector subtraction by subtracting the offset from a current position of the light pattern to compute a next position of the light pattern. This is subject to a conventional step of mapping the coordinates of the camera 110 to the coordinates of the light source 109 or vice versa.

As an example:
Pupil-to-glint vector=(3,7)
current light pattern position=(50,75)
Then:
Next position of the light pattern=(50,75)−(3,7)=(47,68)

Thus vector operations such as addition and subtraction may be applied to compute the position of the light pattern in a coming time step based on an estimated position of the glint and an estimated position of the pupil in a previous time step.

In other embodiments the image processor 101 outputs the offset, e.g. as a two-dimensional vector value, to a loop controller 103 via a loop error estimator that comprises a reference controller 104 and a comparator 105. The reference controller 104 is configured to set a static or a dynamic reference that sets a desired value for the offset e.g. in case a deliberate shift between the position of the pupil and the position of the glint is desired. This may be used to compensate for a difference between the so-called optical axis and the so-called visual axis. In this case, the reference may be adapted dynamically to the offset as shown by dashed line 118.

In yet other embodiments the offset comprised by the offset signal 106 from the image processor 101 is supplied directly as input to the loop controller 103 which in turn outputs the feedback signal 107.

Thus the gaze tracking system 100 comprises a control loop 108 wherein the image processor 101 is coupled to provide a control signal or feedback signal to the light source controller 102.

The computer 107 may be a stationary computer, a laptop computer, a tablet computer or any other type of computer. The display 108 may be any type of computer display as known in the art. It should also be noted that one or both of the control loop 108 and the computer 107 may be integrated in a single computing unit or in a so-called chip-set e.g. for the purpose to integration into a small-sized electronic device such as a smart-phone, tablet or another type of device. The control loop 108 may be implemented in software and run by a computing device.

The light source controller 102 is configured as an interface for controlling the light source to emit the light pattern at desired positions at points in time. The light source controller 102 may be configured as a conventional graphic display controller. Since, compared to most modern systems, only relatively simple graphics functions are required for displaying the light pattern on the light source 109, the graphics display controller for controlling the light source or interfacing with it, may be reduced in functionality compared to a graphics display controller installed in conventional computer. Thereby cost and power consumption may be reduced.

The light source may be embodied as a transparent infrared display e.g. as an Emissive Projection Display e.g. known under the name Kolon by NeoView™.

The image processor may be configured to process the glints as disclosed in the co-pending applications WO10/003410-A1 or WO12/055444-A1 or in U.S. Pat. No. 6,659,611.

The control loop 108 is thus coupled to a sensor in the form of a camera 110 that observes the user's at least one eye and to a controllable actuator in the form of a light source that can emit a light pattern at a desired position. The user's eye and glints thereon is then observed by the camera and the light source is controlled to emit light such that the glint caused by the light source occurs on the user's eye at a predetermined position relative to the eye e.g. relative to a centre of the pupil. The orientation of the eye is thereby observed. In this way the user's point-of-regard can be estimated to be at the desired position, where the light pattern is positioned.

Figure 2:
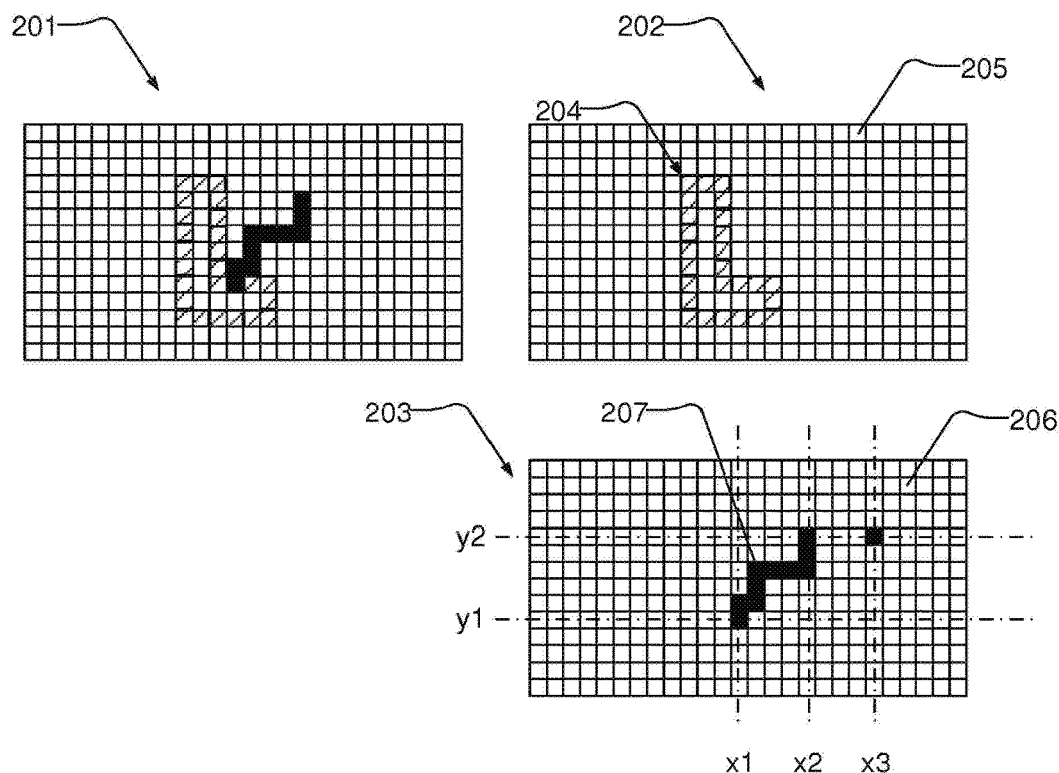
FIGS. 2, 3 and 4 show different light patterns emitted by the light source.

FIG. 2 shows, in a first embodiment, light emitted from light elements of the light source 109 at infrared wavelengths and light emitted from light elements of a computer display at visible wavelengths. The light source 109 constitutes a layer in front of the computer display 108, wherein the light source 109 and the computer display 108 largely spans the same area.

The light elements of the computer display are generally designated by reference numeral 205. The computer display 108 is illustrated by a frame 202 wherein some light elements emits light to display a shape 204 in the form of a capital as illustrated by hatching.

Turning to the light source, illustrated by a frame 203, the light elements of the light source are generally designated by reference numeral 206, wherein light elements that emit light is shown in solid black. Firstly, in this exemplary illustration, the light pattern is generated by one of the light emitting elements at a point in time as illustrated at the position (x3, y2). This light pattern causes a corresponding glint on the pupil of the user. By means of the closed loop, this light pattern is moved from one position to another, one position at a time, to follow the user's gaze. Thereby, the position of the light pattern e.g. at position (x3, y2) is indicative of the user's gaze point at a corresponding point in time.

Secondly, for the purpose of illustration, a trace 207 of gaze points is shown by a solid black path. The trace 207 starts at a position (x2, y2) and ends at a position (x1, y1). In some embodiments the light pattern is displayed at only one position at a time to enable more accurate position determination of the corresponding glint. However, in some embodiments a trace may be displayed by displaying the light pattern at multiple positions at a time, wherein the trace fades at previous positions.

A frame 201 shows a compound representation of the visible light emitted by the computer display 108 and the infrared light emitted by the light source 109.

Figure 3:
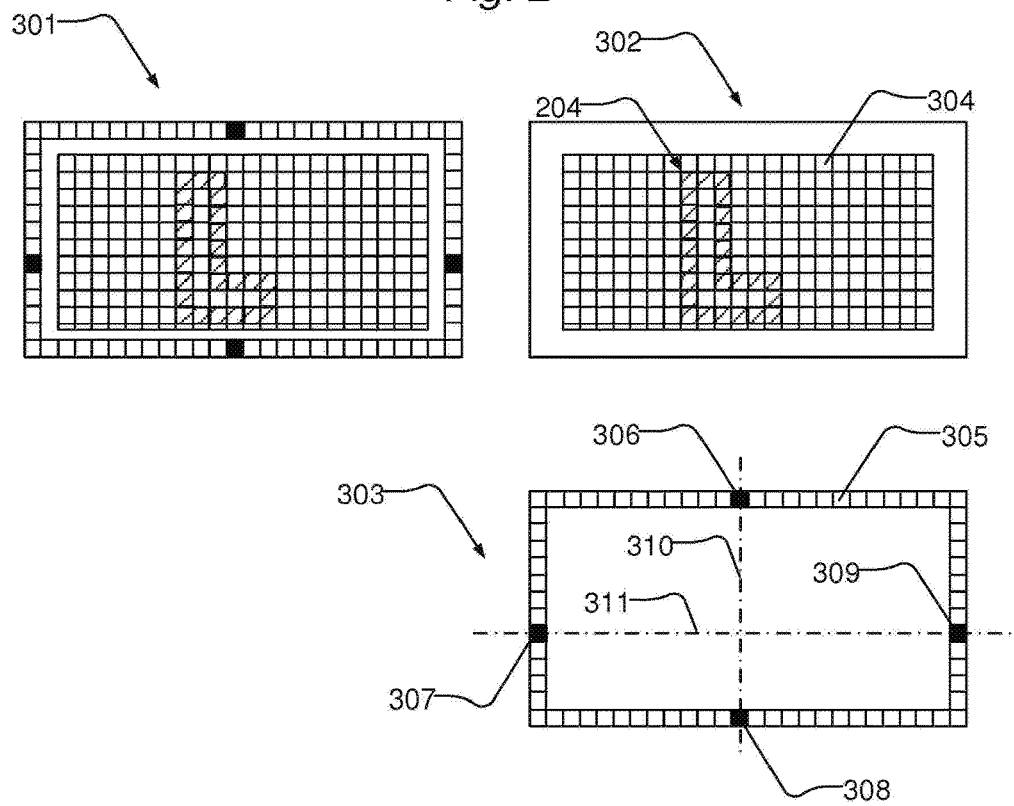

FIG. 3 shows, in a second embodiment, light emitted from light elements of the light source 109 at infrared wavelengths and light emitted from light elements of a computer display 108 at visible wavelengths. In this embodiment, the light source is configured as elongated arrays of light elements arranged along the periphery of the computer display or along one or more edges thereof.

The light elements of the computer display are generally designated by reference numeral 304. The computer display is illustrated by a frame 302 wherein some light elements emits light to display a shape 204 in the form of a capital as illustrated by hatching.

Turning to the light source, illustrated by a frame 303, the light elements of the light source are generally designated by reference numeral 305, wherein light elements that emit light is shown in solid black. Since the light source is arranged adjacent to the computer display, e.g. along the periphery of the computer display, the light pattern is split up to or divided into two or more patterns 306, 307, 308, 309 that are moved under control of the closed loop along transversely arranged line arrays. Thus the light source is configured as line arrays. As shown the light source comprises a pair of horizontally arranged line arrays that are mutually substantially parallel and a pair of vertically arranged line arrays that are mutually substantially parallel. The two pairs of line arrays are arranged at substantially right angles with respect to each other.

The position of the light pattern when detected as glints on an eye can be chosen to be at an intersection of two lines 310 and 311 which can be estimated by the image processor.

The light source may alternatively be configured with a line array of light elements arranged as a round shape such as a circular share or oval shape.

Figure 4:
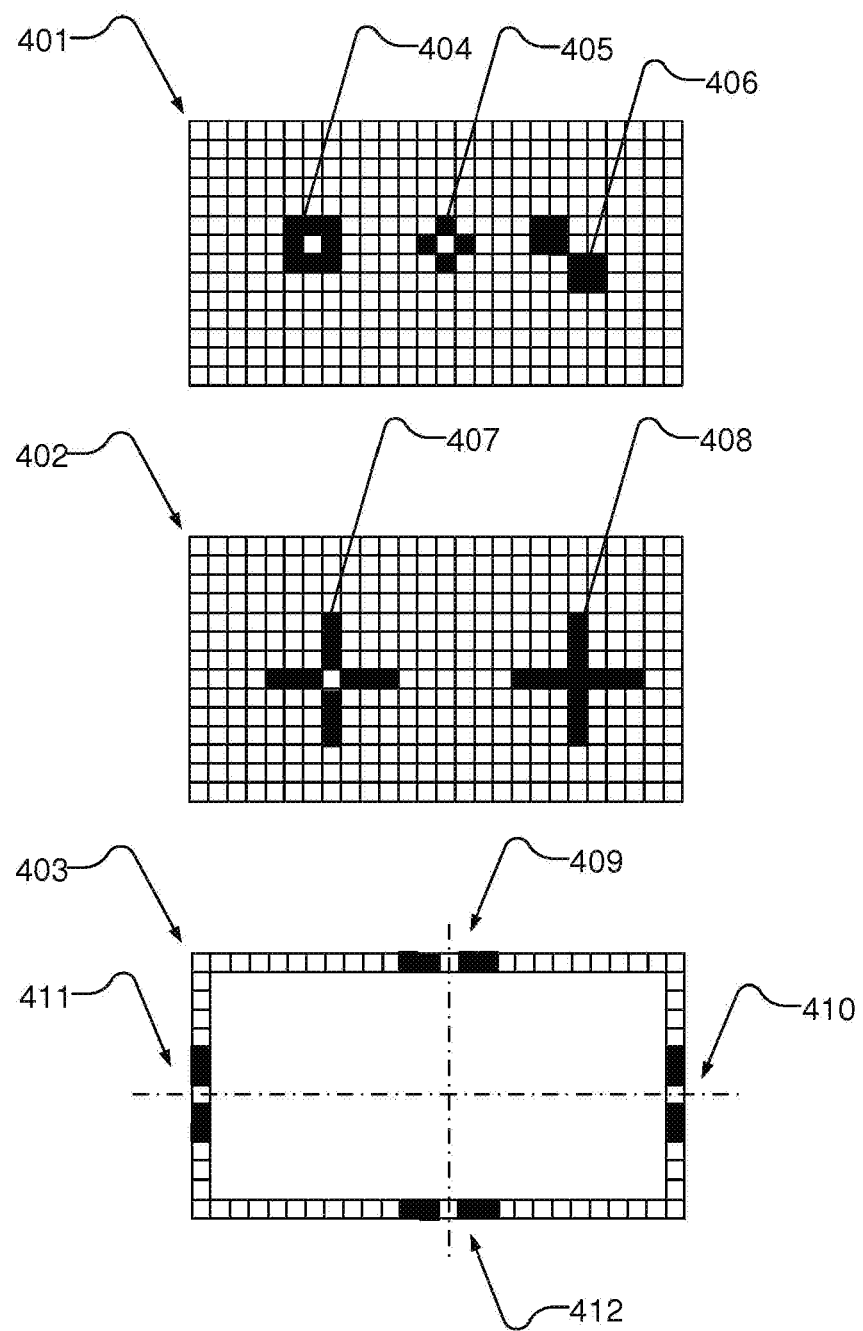

FIG. 4 shows further examples of light patterns. These light patterns can be emitted by the light source e.g. at infrared wavelengths. In a first frame 401 patterns 404, 405 and 406 are shown. The pattern 404 has a square outer shape with a centre hole. The pattern 405 has a circular outer shape with a centre hole. The pattern 406 is composed of two squares that meet at two respective corners.

In a second frame 402 patterns 407 and 408 are shown. The patterns 407 and 408 have the shape of a cross; wherein the pattern 407 has a centre hole and wherein the pattern 408 is solid.

In a third frame 403 a pattern is composed of four sub-patterns 409, 412, 410, 411 each shaped as two rectangles arranged end-to-end, but with a space between them. Sub-patterns 409 and 412 are arranged in the horizontal direction and the sub-patterns 410 and 411 are arranged in the vertical direction.

In some embodiments the sub-patterns 409 and 412 are aligned in a horizontal direction as shown and moved mutually in concert by the closed loop; whereas the sub-patterns 410 and 411 are aligned in a vertical direction as shown and moved mutually in concert by the closed loop.

Figure 5A:
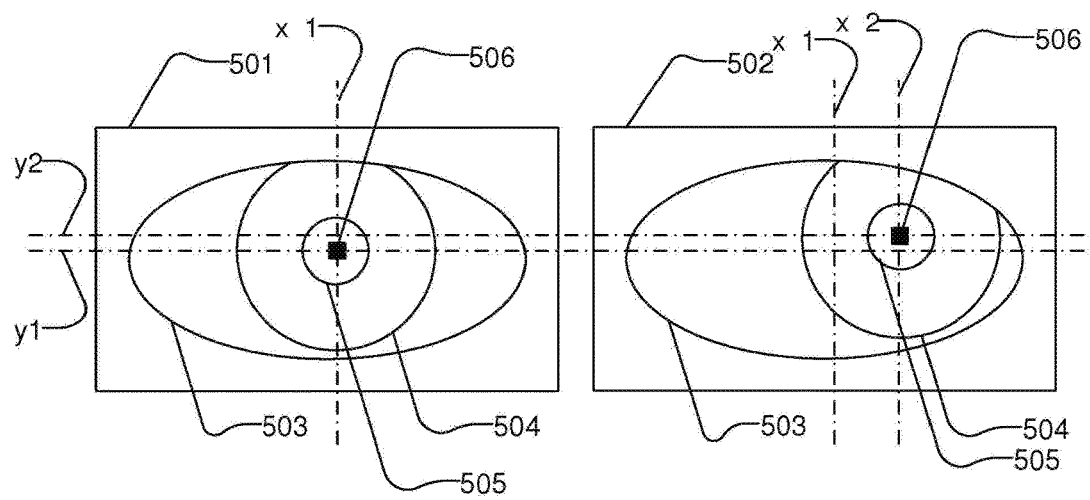
FIGS. 5a and 5b show examples of images of a beholder's eye with glints.

FIG. 5a shows a first example of images of a beholder's eye with glints. The images are recorded by the camera and are processed by cropping to single out one of the user's eyes. In this first example the light pattern emitted by the light source is shaped as a square dot.

A first image 501 shows an eye socket 503, the iris 504 and the pupil 505. Additionally, the first image 501 shows a glint 506 which is a reflection of light on the cornea (not shown) from the light pattern emitted by the light source. Image 501 illustrates a situation wherein the closed loop gaze tracker has moved the position of the light pattern such that the glint 506 occurs in the centre of the pupil 505.

Further, it is noted that the pupil 505 and the glint 506 are located at a first position (x1, y1), which appears to be at a position where the user is looking at a point straight in front of his eye. It should be noted that the dashed lines designated y1, y2, x1 and x2 are not part of the image recorded by the camera, but they are shown to emphasize the movement of the iris 504 and the pupil 505.

A second image 502 shows the pupil and the glint 506 at a second position (x2, y2) wherein the user has moved his eyes and is looking a bit upwards and to one side. Also in the second image 502 it is noted that the closed loop gaze tracker has moved the position of the light pattern such that the glint 506 occurs in the centre of the pupil 505.

Thus, it is illustrated that the closed loop gaze tracker tracks the movement of the eye, or rather the pupil 505, by moving the position of the light pattern such that the glint on the cornea from the light pattern occurs in the centre of the pupil. The closed loop may also track the movement of the pupil 505 by moving the position of the light pattern such that the glint on the cornea occurs decentred by a predefined static offset or by a dynamically adjusted offset which may be adapted to the offset e.g. to an offset vector and/or to the position of the pupil relative to the eye socket or another spatial feature that can be used as a reference point.

Figure 5B:
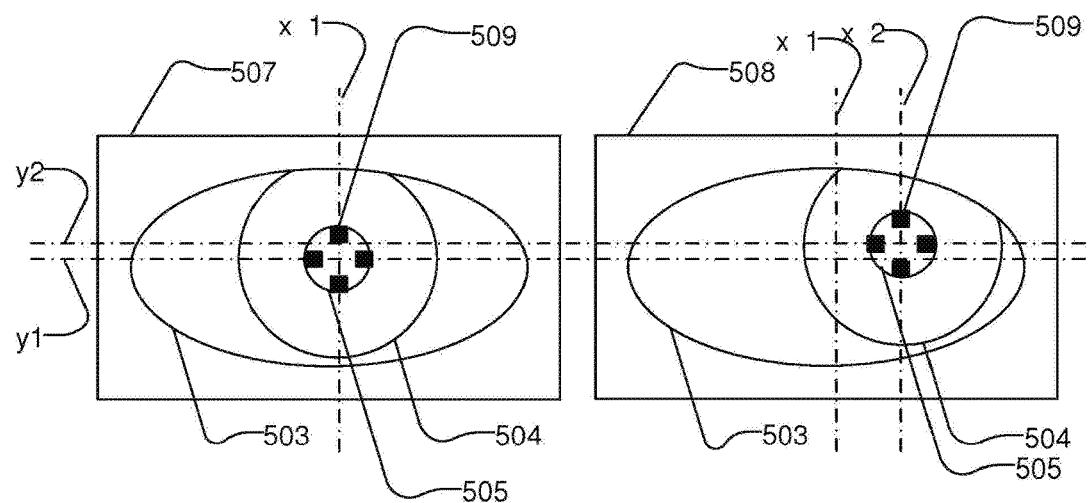

FIG. 5b shows a second example of images of a beholder's eye with glints. A third image 507 also shows the eye socket 503, the iris 504 and the pupil 505. In the third image the glint comprises four glints generally designated 509. The glints are caused by a corresponding 'four-dots' light pattern emitted by the light source. Image 507 illustrates a situation wherein the closed loop gaze tracker has moved the position of the light pattern such that the glints 509 occur in the centre of the pupil 505. Here, the position of the glints is chosen to be a geometric centre of the glints e.g. a geometrical point of gravity. In the third image the pupil and the position of the glints are shown to be at the position (x1, y1).

A fourth image 508 shows the pupil and the glints at a second position (x2, y2) wherein the user has moved his eyes and is looking a bit upwards and to one side. Also in the fourth image 508 it is noted that the closed loop gaze tracker has moved the position of the light pattern such that the glints 509 occur in the centre of the pupil 505.

Figure 6:
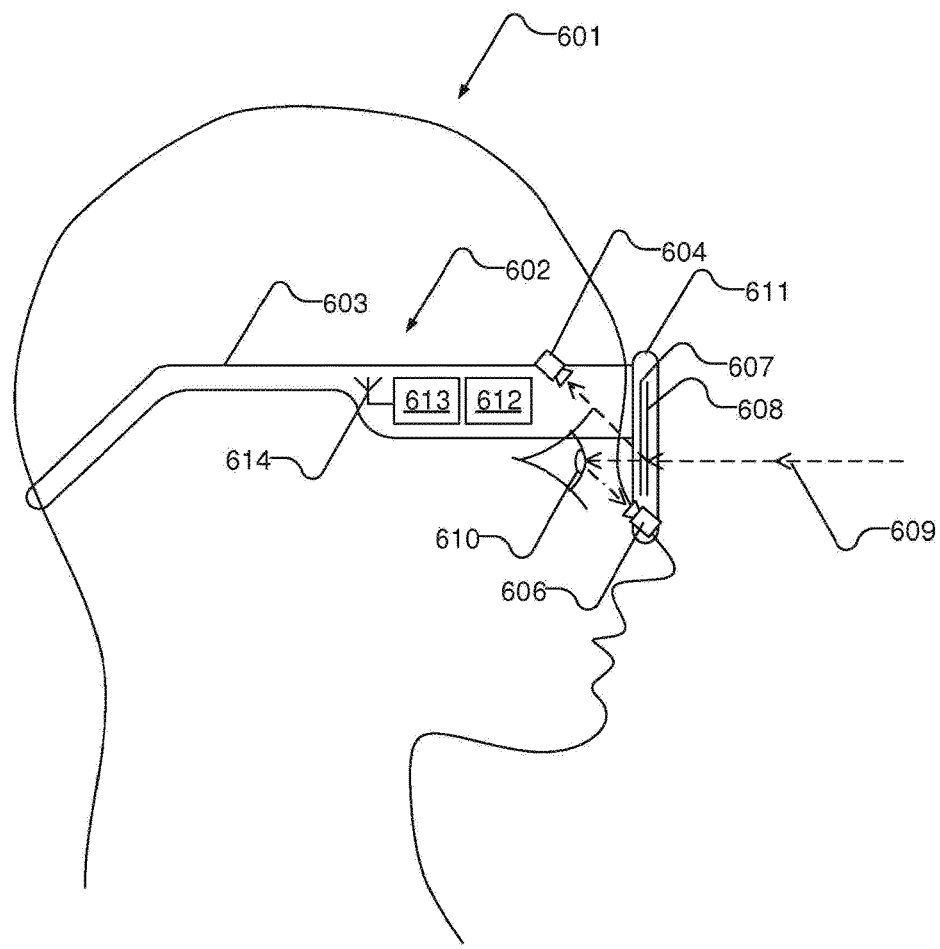
FIG. 6 shows a block diagram of a gaze tracker embodied as a Wearable Computing Device.

FIG. 6 shows a block diagram of a gaze tracker embodied as a Wearable Computing Device. The wearable computing device generally designated 602 is worn by a human being 601, also denoted a user, as a pair of glasses by means of side bars 603 connected to a frame 605. The frame holds a beam-splitting layer 607 and a transparent display 608. Additionally, the frame may hold one or more protective screens to protect the display 608 and/or the beam-splitting layer 607 from scratches and the like.

The transparent display 608 displays the pattern of light as described in detail above. Thus, the transparent display 608 operates as the controlled light source.

The beam-splitting layer 607 splits a beam of light illustrated by dashed line 609 from in front of the user into a first direction towards the user's eye and into a second direction towards a camera 604. The beam-splitting layer 607 may comprise a multitude of beam-splitters each configured with an inclined half-mirror.

The camera 604 is integrated with or mounted on a side bar 603 and is pointed towards an inner side (i.e. the user's side) of the beam-splitting layer 607 to capture images compounded from light from a scene in front of the user and from light emitted by the transparent display 608. Thus, since the closed loop gaze tracker moves the pattern of light on the transparent display 608 to make a corresponding glint on the user's cornea coincide with the user's pupil, the camera 604 can capture an image of a scene in front of the user, wherein the light pattern coincide with the point or object the user is gazing at. Images from the camera 604 are supplied to the processor 612. These images contains image information for computing an estimate of what object the user is looking at in the scene in front of him. The camera 604 is also denoted a scene camera.

In some embodiments the transparent display emits the light pattern at infrared wavelengths and the camera 604 is sensitive to infrared light. In other embodiments the transparent display emits the light pattern at visible wavelengths and the camera 604 is sensitive to visible light.

The user sees through the transparent layer 607 as indicated by the dashed line 609. Also, the user sees through the transparent display 608, which operates as the controlled light source.

Images of the user's eye are captured by a camera 606 which is also denoted an eye camera.

In some embodiments the wearable computing device 602 comprises a scene camera (not shown) which captures scene images of any scene in front of the user and supplies the scene images to the processor 612. The camera may be integrated with or mounted on the frame 611. Such a camera may replace the camera 604, albeit without the option of capturing image information from the transparent display. In some embodiments such a camera is provided in combination with a so-called non-see-through display, which displays an image of the scene as captured by the scene camera.

The processor 612 is coupled to a radio transceiver 613 for establishing radio communication via an antenna 614 to other devices such as computers, smart-phones etc.

Figure 7:
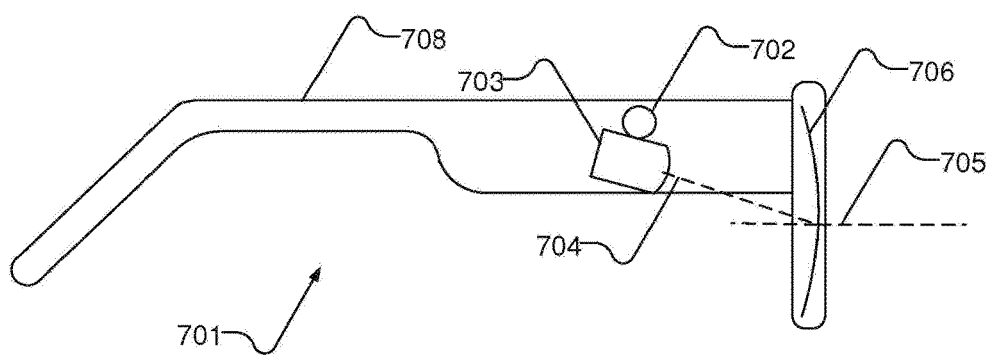
FIG. 7 shows a light source on a controllable pivot mount and configured to point focussed light onto a screen.

FIG. 7 shows a light source on a controllable pivot mount and configured to point focussed light onto a screen. In this embodiment of a wearable device generally designated 701 the controllable light source comprises a partially reflective screen 706, such as a half-mirror, and a focussed light source 703, such as a diode laser or LED source with an appropriate optical system (not shown), and a computer controllable mount 702 that can point a light beam 704 from the focussed light source 703 to a position on an inner side of the screen 706. The light beam 704 is reflected on the inner side of the partially reflective screen 706 and further on the cornea of a user's eye such that a corresponding glint can be captured by a camera (not shown).

A light beam 705 from a scene in front of a user wearing the wearable device 701 is transmitted through the partially reflective screen 706 from an outer side thereof and onto the cornea of the user's eye.

In general a half-mirror designates layers, screens, films, coatings, etc. that reflect a fraction of the light incident on the half-mirror and transmits another fraction of light through the half-mirror. The fraction of light reflected and the fraction of light transmitted may be selected and may be different from a 50/50 fraction excluding optical losses e.g. about 25% may be reflected and about 75% may be transmitted excluding optical losses.

Figure 8:
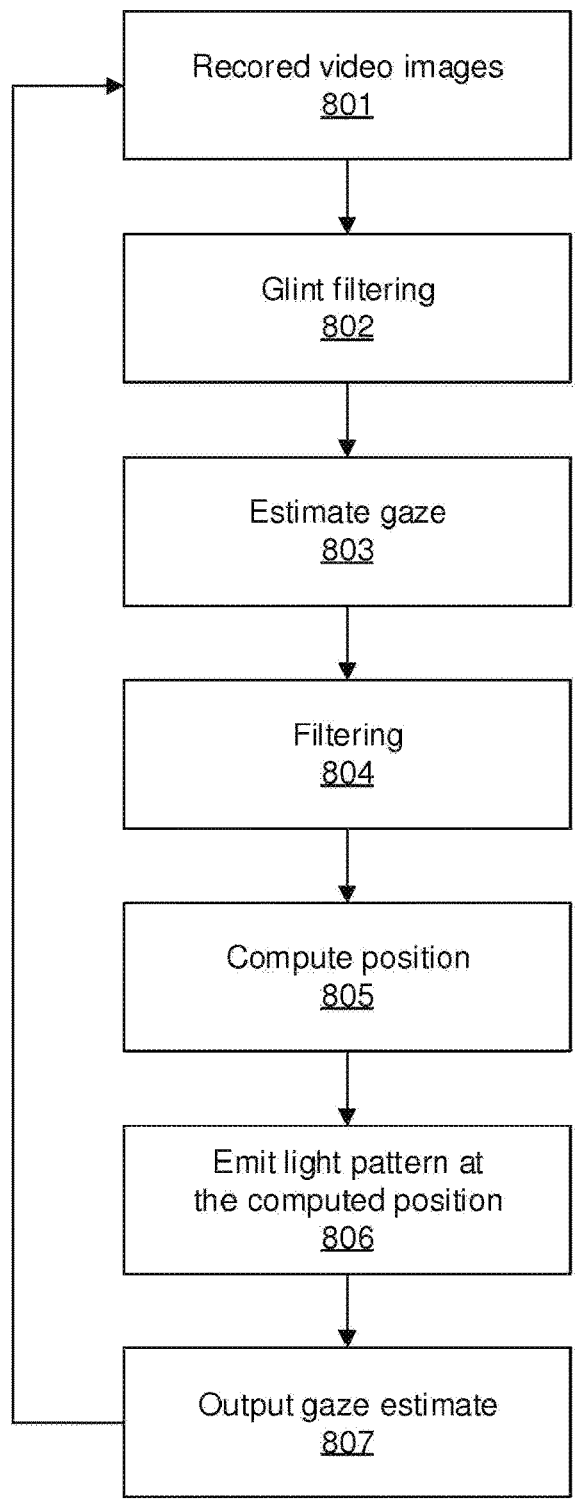
FIG. 8 shows a flowchart for the gaze tracking method.

FIG. 8 shows a flowchart for the gaze tracking method. In a step 801 of the method video images of a human being's eye is captured. The video images are then subject to glint filtering in step 802. The step 802 of performing glint filtering is optional, but may be necessary or expedient to filter out glints which are not caused by the controllable light source. Methods for performing glint filtering are known in the art of processing images for estimating gaze.

In a step 803 of the method video images of the eye with cornea and the pupil and one or more glints are processed by image processing to estimate gaze in the form of offset vector values representing a distance, e.g. a two-dimensional distance, between the pupil the one or more glints caused by the light pattern. The offset vector may be computed for each video image in a sequence of video images or for every second or third video image or at another rate which may be chosen programmatically or dictated by hardware limitations.

Then an optional step 804 of the method performs filtering of values of the offset vector. The filtering is configured to improve performance of the closed loop gaze tracker such that eye movements are more reliably tracked and/or more accurately tracked. The filtering may involve predictive filtering or low-pass filtering.

In a step 805 a position for the light pattern to be emitted is computed. This position may be encoded as a control signal to the light source. In case the light source is a display e.g. a transparent display the control signal may be a conventional digital display signal. Step 805 may also involve computing a presentation of the light pattern at the computed position.

In a subsequent step 806 the light source emits the light pattern at the computed position.

In step 807 the computed position or a transformed value therefrom is output as a gaze estimate. The computed position or a transformed value therefrom is output via a software interface and/or via a hardware interface.

In some embodiments the gaze estimate is obtained by capturing an image of the light source, with the light pattern, and processing the image to derive the gaze estimate from a position of the light pattern in the image.

In the above, by 'optional' should be understood that the step 802 and/or step 804 may be omitted in embodiments of the claimed invention or they may be selectively performed.

The claimed gaze tracker tracks gaze in the form of an estimated point-of-regard, which may correspond to a point coinciding with a gaze vector; albeit the gaze vector is not explicitly estimated. In some embodiments the gaze vector or its direction may be explicitly estimated.

The invention claimed is:

1. A gaze tracker comprising:
an image processor configured to:
process video images of at least one eye of a being, wherein a predetermined spatial feature of the at least one eye and a glint on the being's at least one eye caused by a light source is recorded, and
generate an offset signal representing an offset between a position of the predetermined spatial feature and a predetermined position with respect to the glint; and
a light source controller configured to output a control signal to a light source that is configured to emit a light pattern from a selectable position among a multitude of preconfigured positions towards the being's at least one eye;
wherein the light source controller is configured to move the light pattern, in response to a feedback signal;
wherein the image processor and the light source controller are coupled in a control loop providing the feedback signal from the offset signal;
wherein the light source displays the light pattern at a location representing the being's point-of-regard; and
wherein an output indicative of a gaze vector or point-of-regard is generated from the feedback signal.

2. A gaze tracker according to claim 1, wherein the light source is configured as a first display comprising light emitting elements emitting infrared light and arranged regularly in an array structure extending over or along a preconfigured area.

3. A gaze tracker according to claim 2, wherein the preconfigured area is aligned with an area of a second display which is a computer display screen for displaying visible light.

4. A gaze tracker according to claim 3, wherein the first display and the second display are integrated to form a dual wavelengths display.

5. A gaze tracker according to claim 1, wherein the light source comprises a focused light source and a controllable pivot mount arranged in combination to controllably, via the feedback signal, point focused light onto a screen that is arranged in front of the eye such that a glint is observable on the eye.

6. A gaze tracker according to claim 1, configured to filter the video images to identify one or more glints that are likely to originate from the light pattern, and wherein the predefined position relative the glint is computed relative to identified one or more glints that are identified to be likely to originate from the light pattern.

7. A gaze tracker according to claim 1, comprising a loop controller configured to filter the offset signal computed from processing the video images and outputting the feedback signal as a result of the filtering.

8. A gaze tracker according to claim 1, comprising a camera arranged to record images of a being's eye such that a predetermined spatial feature of the being's eye and a glint caused by the controllable light source is recorded.

9. A gaze tracker according to claim 1, wherein the gaze tracker is configured to be worn as a wearable device and wherein the light source comprises light emitting elements arranged in an array structure extending over a preconfigured area which largely covers the field-of-view of the eye at least for some movements of the eye within the eye-socket.

10. A gaze tracker comprising:
an image processor configured to:
process video images of at least one eye of a being, wherein a predetermined spatial feature of the at least one eye and a glint on the being's at least one eye caused by a light source is recorded, and to generate an offset signal representing an offset between a position of the predetermined spatial feature and a predetermined position with respect to the glint; and
a light source controller configured to output a control signal to a light source that is configured to emit a light pattern from a selectable position among a multitude of preconfigured positions towards the being's at least one eye;
wherein the light source controller is configured to move the light pattern, in response to a feedback signal;
wherein the image processor and the light source controller are coupled in a control loop providing the feedback signal from the offset signal;
wherein the light source displays the light pattern at a location representing the being's point-of-regard;
wherein an output indicative of a gaze vector or point-of-regard is generated from the feedback signal; and
wherein the gaze tracker is configured to be worn as a wearable device, comprising:
a scene camera with an image sensor;
a screen, with a first layer and a second layer, arranged in front of the wearer's eye, with an inner sider facing towards the eye;
wherein the light source is configured as a transparent display and arranged as the first layer of the screen;
wherein the second layer comprises a beam-splitting layer that splits light from at least some directions in front of the screen to impinge on the eye and on an image sensor of the scene camera; and
wherein the scene camera is pointed towards the inner side of the screen.

11. A gaze tracker according to claim 1, wherein the output is generated via a video camera arranged with a field-of-view at least partially covering the light source.

12. A computer-implemented method for gaze tracking, comprising the steps of:
recording video images of a being's eye such that a predetermined spatial feature comprising a pupil of the being's eye and a glint on the being's eye caused by a light source are recorded;
processing the video images to compute an offset signal between the position of the predetermined spatial feature and a predetermined position with respect to the glint;
by means of the light source, emitting light from a light pattern at a location selected among a multitude of preconfigured locations of light patterns towards the being's eye; wherein the location is controlled by a feedback signal to represent the being's point-of-regard to represent the beholder's point-of-regard;
controlling the location of the light pattern from one location to another location among the preconfigured locations of light patterns, in response to the offset signal, such that the predetermined position with respect to the glint caused by the light source tracks the predetermined spatial feature of the being's eye;
generating an output indicative of a gaze vector or point-of-regard from the feedback signal; and
wherein the preceding steps are repeated to establish a control loop with the location of the light pattern being controlled via the feedback signal.

13. A computer-implemented method according to claim 12, wherein the location of the light pattern is controlled via the feedback signal by sequentially addressing and activating different sets of light emitting elements among an array of light emitting elements arranged in a fixed structure.

14. A computer-implemented method according to claim 12, comprising:
filtering the offset signal computed from processing the video images by a loop controller and outputting the feedback signal as a result of the filtering.

15. A computer-implemented method according to claim 12, wherein the light pattern is emitted at an infrared wavelength and concurrently a visible user interface is displayed on a display screen.

16. A computer-implemented method according to claim 12, comprising:
filtering the video images to identify one or more glints that are likely to originate from the light pattern, and computing a predefined position relative to the one or more glints that are identified.

17. A data processing system comprising a computer device having stored thereon program code means adapted to cause the data processing system to perform the steps of the method according to claim 12, when said program codes means are executed by the computer device.

18. A non-transitory computer program product comprising program code means adapted to cause a data processing system to perform the steps of the method according to claim 12, when said program code means are executed on the data processing system.

19. A non-transitory computer program product according to claim 18, comprising a computer-readable medium having stored thereon the program code means.

20. The gaze tracker of claim 1, wherein the predetermined spatial feature is the pupil of the at least one eye.

* * * * *

UNITED STATES PATENT AND TRADEMARK OFFICE
CERTIFICATE OF CORRECTION

PATENT NO. : 10,234,940 B2
APPLICATION NO. : 15/548506
DATED : March 19, 2019
INVENTOR(S) : Diako Mardanbegi et al.

It is certified that error appears in the above-identified patent and that said Letters Patent is hereby corrected as shown below:

In the Claims

In Claim 10 at Column 17, Line 28, change the word "sider" to "side".

Signed and Sealed this
Fourteenth Day of May, 2019

Andrei Iancu
*Director of the United States Patent and Trademark Office*